Figure 1:
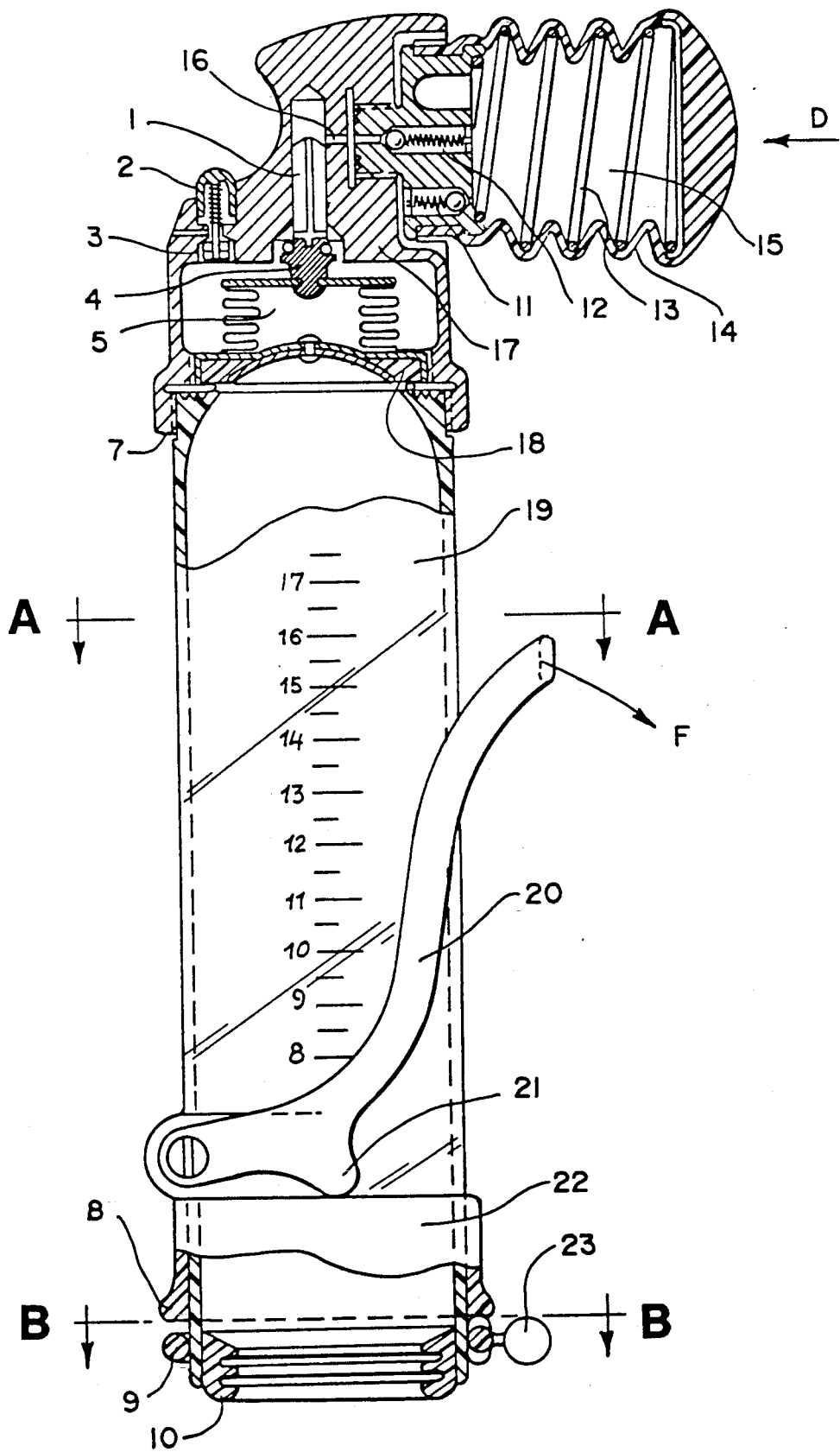

United States Patent

Matejevic et al.

[11] Patent Number: 5,115,800
[45] Date of Patent: May 26, 1992

[54] APPARATUS FOR ACHIEVING AND MAINTAINING PENIS ERECTION

[75] Inventors: Nenad Matejevic; Dragica Matejevic, both of Beograd, Yugoslavia

[73] Assignee: BVK Konsalting, Yugoslavia

[21] Appl. No.: 577,913

[22] Filed: Sep. 5, 1990

[30] Foreign Application Priority Data

Sep. 11, 1989 [YU] Yugoslavia .............. 1740/89

[51] Int. Cl.⁵ .............................................. A61F 5/41
[52] U.S. Cl. .............................................. 600/39
[58] Field of Search ............ 128/79; 119/14.47, 14.48, 119/14.49, 14.50, 14.51, 14.52, 14.53; 604/315, 316, 346, 349

[56] References Cited

U.S. PATENT DOCUMENTS

| | | | |
|---|---|---|---|
| 1,126,920 | 2/1915 | Uebler | 119/14.47 |
| 2,874,698 | 2/1959 | Sell | 128/79 |
| 3,744,486 | 7/1973 | Wilson | 128/79 |
| 4,718,411 | 1/1988 | Stewart | 128/79 |
| 4,738,673 | 4/1988 | Shepard | 604/349 |
| 4,741,329 | 5/1988 | Marcune | 128/79 |
| 4,753,227 | 6/1988 | Yanuck, Jr. | 128/79 |

Primary Examiner—Cary E. O'Connor
Attorney, Agent, or Firm—Wood, Phillips, Van Santen, Hoffman & Ertel

[57] ABSTRACT

An apparatus for achieving and maintaining penis erection—based on the effect of a reduced air pressure on the external surface of the penis comprises a transparent tube (19) provided with a head (17) with automatic regulator (1-4) of air discharge from the tube and a vacuum pump (15). When the penis is inserted into the tube (19) and when the bellows (14) of the pump (14) are periodically depressed, the penis will, under the effect of a reduced air pressure, reach its erection. By shifting a lever (20) in the F direction, an elastic ring (9) will be slipped from the neck of the tube (19) onto the base of penis the in erection and the erection will be maintaining during the intercourse. Just before the ejaculation, the elastic ring (9) will be quickly disconnected and the semen will be normally expelled before the penis is taken out of the vagina.

9 Claims, 3 Drawing Sheets

APPARATUS FOR ACHIEVING AND MAINTAINING PENIS ERECTION

The invention relates to an apparatus for achieving and maintaining penis erection.

This invention is directed to the problem of the inability of achieving and maintaining penis erection in men, i.e. it enables a natural impregnation of women by men who are unable to achieve an erection of penis with sufficient firmness so to be able to penetrate into the vagina of a woman or who are unable to maintain the erection long enough for a successful intercourse.

Inability of achieving the penis erection in men is solved in a number or known ways, such as: by use of special injections, by use of semi-stiff condomes, by incorporation of eleastic inserts into the body of penis, by incorporation of cavernous tubular inserts in the body of the penis which are then filled with a liquid for the purpose of achieving the firmness of the penis, etc.

Beside the mentioned methods, this problem is solved by application of the known method by which a lower air pressure is applied onto the body of the penis—for the purpose of achieving erection, in combination with the application of an elastic ring at the base of the penis—for the purpose of maintaining the erection.

The apparatuses used for this purpose are still in the developing and design-improving stage depending on the demands and requirements of the patients.

Satisfactory results have been achieved so far which, by improvement of these apparatus, are to become more effective and especially easier for handling and use.

The main shortcomings of these apparatuses are:

1. They do not provide automatic regulation of the quantity of the air to be discharged from the tube (into which the penis is inserted) depending on the level of the erection during the process of achieving erection of the penis.

2. They do not provide the possibility of applying the lower air pressure onto the whole external surface of the penis (especially onto the part at the very base of the penis).

3. The elastic ring for tightening of the base of the penis cannot be quickly enough slipped from the neck of the apparatus onto the base of the penis after achieving erection.

4. The units with the same dimensions of the tube opening cannot be universelly used for the organs of different diameters.

5. It is not possible to hold simultaneously the free end of the apparatus and operate the pump with one hand to have the other hand free for operating the mechanism for slipping the elastic ring for tightening the base of the penis.

6. It is not possible to separate physically all the sensitive parts of the apparatus from the tube into which the penis is inserted for the purpose of easy washing and cleaning of the tube from inside.

7. It is not possible to use more than once the same elastic ring for tightening the base of the penis.

The problem to be solved by the present invention is to provide an apparatus as set out above which may be easily and safely used and imitates as far as possible the physiological processes occuring during the natural erection of the penis.

This problem is solved by the apparatus as set out in claim 1. Further advantageous developments and embodiments are set out in the subsidiary claims.

In designing this apparatus of the invention a four-year experience of work with patients using the known apparatus for this purpose was used—considering especially the stricter medical requirements, in order to acquire the truest possible imitation of physiological processes occuring the natural erection of the penis. The problem has been solved, from the medical point of view, by the most acceptable principle, i.e. by application of a reduced air pressure onto the external surface of the penis. Medically, application of this principal is harmless to any of the human body functions. The apparatus is easily used. The results of its use are exceptional and this way of treatment is gladly accepted by patients. From the medical point of view erection is simply turgidity (firmness) of the penis due to the pressure of the blood filling the cavernous tissue of the penis. If there is no such blood pressure in the penis (due to any reasons) or, if the existing blood pressure is not sufficient, the erection cannot be achieved.

The principle of the functioning of the apparatus for achieving and maintaining the erection of the penis is very similar to the natural physiological processes occuring in the body of a man. Namely, the effect of the created subpressure on the external surface of the penis causes a relative increase of the blood pressure in the penis itself what then causes filling of the cavernous tissue of the penis with blood, same as in the natural process. In other words, due to the effect of the air subpressure on the external surface of the penis, it starts expanding in volume, the blood fills the cavernous erectile tissue and the erection is achieved. After having achieved the erection, the elastic ring is slipped onto the base of the penis to prevent the backflow of the blood from the penis for the purpose of the maintaining the achieved erection during the intercourse. This ring for tightening the base of the penis can be easily removed (released) by pulling the little ball fitted at the ends of the ring, at any moment required and without having the ends of the ring, at any moment required and without having to take the penis out of the vagina.

This invention is, from the engineering-medical point of view, a wholly new design resulting from the taking into consideration of the stricter medical requirements, in order to provide the truest possible imitation of the natural physiological processes occuring during the natural erection if the penis. All the shortcomings of the known apparatus have been eliminated by this design.

In order to meet the technical medical requirements during the application of the lower pressure of the air onto the penis, an automatic regulator for the air discharge from the tube is provided which operates in response to the decreasing air pressure in the tube, i.e. on the level of the achieved erection.

Namely, in the beginning phase of the process of making the erection, when the penis can take in proportionally a big quantity of blood in a unit of time, it is necessary to have a bigger quantity of air discharged from the tube to provide a quick expansion of the penis base tissue (the part which is the most sensitive to the effect of the air subpressure) and thus obtain its closing upon the front-labyrinth elastic seal ring, i.e. to provide a good sealing between the neck of the tube and the seal ring what is essential for the further development of the penis erection achieving process.

In the second phase of this process, the cavernous tissue all over the penis length receives blood, i.e. gets filled. This phase of making the erection must, for physiological reasons, run slowly to enable the cavernous tissue of the penis to absorb blood gradually and wholly and, the lower the air pressure in the tube is (i.e. the higher the level of filling of the cavernous tissue with blood in the penis is), the slower this phase must run.

In the third, final phase of this procedure—i.e. when the subpressure in the tube reaches the lowest (prescribed) value, the sucking of the air out of the tube must fully and safely stopped. The penis is kept in such 'environment' until it has reached its full length, i.e. until it has achieved a full erection.

All phases of the procedure for achieving the erection of the penis according to the presented programme must be done faultlessly by the use of the air discharge regulator provided within this apparatus.

Adequate design of the tube of this apparatus ensures that the lower air pressure, during the phase of making the erection, acts on the whole external surface of the penis. Namely, the neck of the tube is made narrower by the front labyrinth seal so that the penis, after entering through the seal ring, has enough free space all around its external surface inside the tube from which the air is sucked out by the pump, enabling a full and unhindered erection of the penis (in all directions).

The problem of hygiene has been solved by the fact that the tube is connected to the head of the apparatus by means of a threaded connection, so that these components an be easily disconnected. Once disconnected from the apparatus, the tube can be readily washed with water and ither agents as it does not contain any sensitive mechanisms or parts that could be damaged by water or other washing agents.

This apparatus is foreseen exclusively as an individual personal aid. It can be equally used both by the left-handed and the right-handed men, depending on which side is the pump in relation to the lever, what can be easily adjusted by turning of the tube in relation to the head of the apparatus. A tube of only one size may be used for penises of all diameters by simply using an elastic seal ring of appropriate inner diameter.

Figure 2:
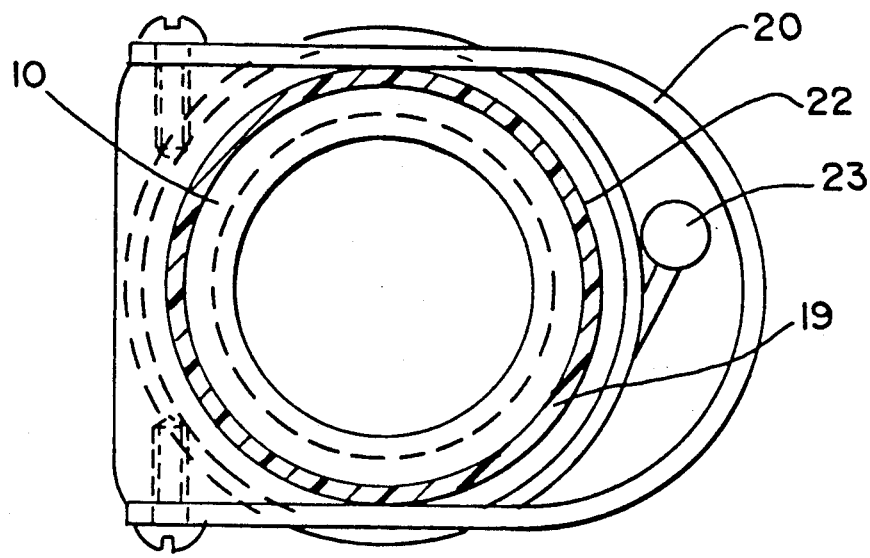
Figure 3:
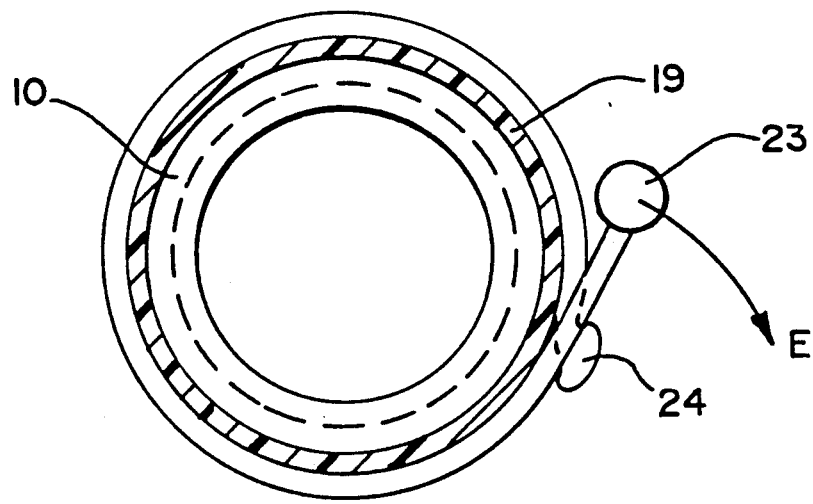
Figure 4:
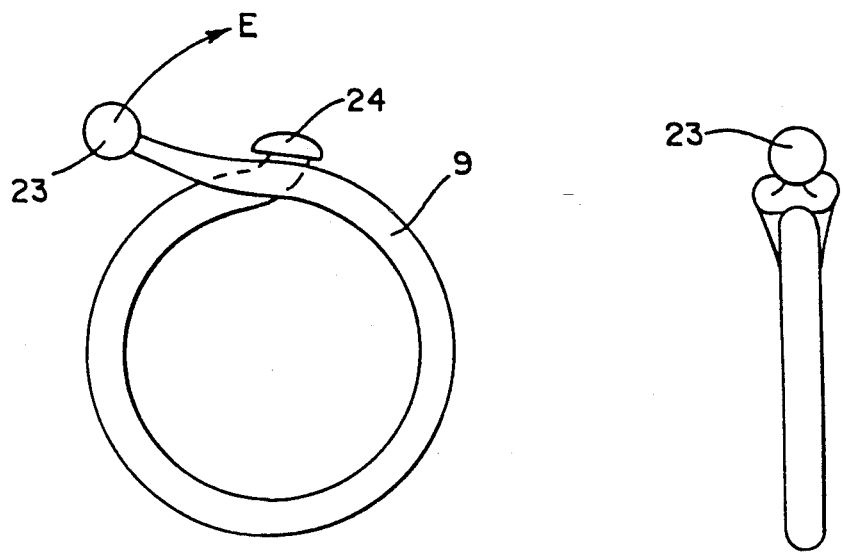
Figure 5:
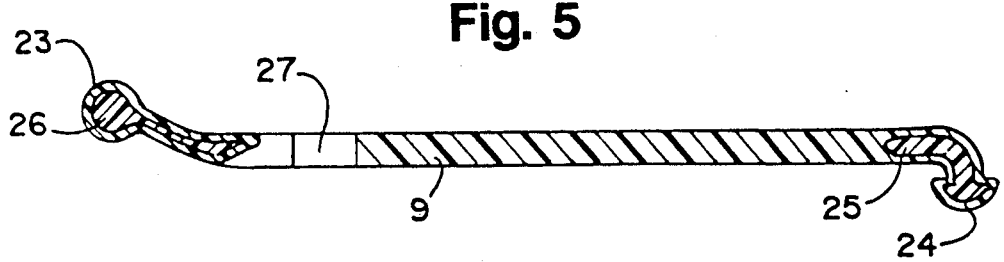
Figure 6:
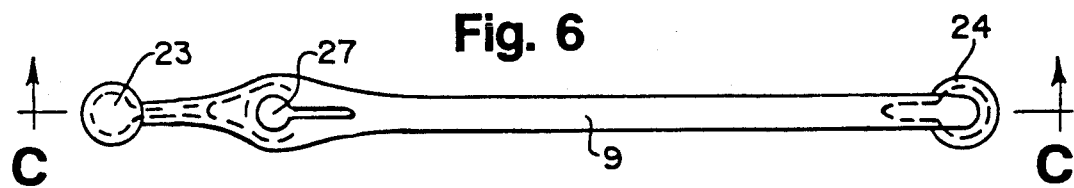
Figure 7:

The invention will be described in more detail on the base of an embodiment of the apparatus shown in the drawings wherein:

FIG. 1 is a partial cross-sectional view of an embodiment of apparatus according to the invention, FIG. 2 a cross-section view along the lines A—A in FIG. 1, FIG. 3 a cross-section view along the lines B—B in FIG. 1, FIG. a top and side view of the elastic ring for tightening the base of the penis, FIG. 5 a cross-sectional view of the unlocked ring of FIG. 4 along the lines C—C in FIG. 6, FIG. 6 a top view of the unlocked ring of FIG. 4, FIG. 7 cross-sections of the ribbon forming the ring of FIG. 4 respectively along the length of the ribbon as shown in FIG. 6.

In FIG. 1, an embodiment of the apparatus is shown in partial section. The apparatus consists of the one-piece transparent tube 19, the head 17 of the apparatus and a bellow pump 15 which are interconnected by means of thread connection fitted with elastic rings.

The tube 19 of the apparatus is a transparent tube of an uniform diameter which is fitted at one end (forming the neck of the tube through which the penis is inserted) with a front-labyrinth seal 10 which is made of elastic material. In order to make it possible that a tube 19 of only one size can be used for penises of all diameters, removeable elastic seal rings 10 of different inside diameters may be provided. The seal ring 10 is easily fitted by simply pressing by hand into the neck of the tube 19. The size of the inside diameter of the seal ring 10 is selected according to the need—depending on the diameter of the penis in erection.

By the design of the sealing ring, the problem of sealing the neck of the tube 19 safely at its contact with the base of the penis has been solved by a combination of frontal (face) and labyrinth sealing with one piece of elastic material which forms the sealing ring 10. On the outside of the neck of the tube 19 is an elastic ring 9 for tightening the base of the penis and a slidable bushing 22 for slipping the elastic ring from the neck of the tube. The bushing 22 is moved by means of a lever 20 for quick slipping of the elastic ring 9 from the neck of the tube.

The elastic ring is formed by an elastic ribbon of a round section (FIG. 4-7), which is fitted with a small ball 23 and a profiled opening 27 at one end and with a semi-rounded small head 24 at the other end. When locked, the seal ring is released (removed from the penis by pulling manually the little ball 23 in the E direction (FIG. 3). The elastic ring 9 can be locked again by fitting its little head 24 into the opening 27 at the other end of the elastic ribbon.

The problem of quick slipping of the elastic ring 9 for tightening the base of the penis from the tube neck onto the base of the penis is expectionally important for maintaining the achieved erection of the penis because, when this ring is shifted form the tube neck onto the base of the penis, the functioning of the seal ring 10 is always disturbed for a short period of time and some of the outside air gets into the tube. In order to secure the least possible penetration of the outside (undesirable) air into the tube 19, this procedure must be the shortest possible.

However, this problem has been successfully solved by the application of the double lever 20 which, when shifted by hand (in the F direction, FIG. 1), pushes the bushing 22 with its two projections (21) and the bushing with its head (8) pushes the elastic ring 9 until it slips from the neck of the tube 19 onto the base of the penis and tightens it at the moment when the penis is in a full erection. This procedure is done very quickly during the use of the apparatus (about 1 sec.).

The other end of tube 19 is provided with a thread connection 7, by which it is connected to the head 17 of the apparatus.

The head 17 of the apparatus connects the tube 19 with the bellow pump 15. It consists of a profiled piece of material which houses an automatic air discharge regulator 1, 4, 5, a filter 18 and a valve 2, 3 for letting the air into the tube.

The regulator of air discharge from the tube 19 consists of an elastic air-tight bellows 5 which hold air (or some other gas) under normal atmospheric pressure. The bellows 5 are tightly connected with the valve 4 for cutting off air discharging from the tube 19—if the elastic bellows increase their height, what happens when the subpressure (due to the operation of the pump 15) reaches its lowest permitted value in the tube 19. In the extension of the valve body, the piston of the regulator 1 is disposed, which by its head edge closes or opens the borehole 16 if the bellows change their height due to the change of the air pressure in the tube 19 thus regulating the discharge of the air from the tube 19. This regulation of air discharge from the tube 19 functions fully automatically and it fully meets the technical medical requirements during the application of the lower pressure of the air onto the penis in that the automatic regulator 1, 4, 5 of air discharge from the tube 19 operates depending on the lower air density in the tube 19, i.e. on the level or the achieved erection. Namely, in the beginning phase of the process of making the erection, when the penis can take in proportionally a big quantity of blood in a unit of time, it is necessary to have a bigger quantity of air discharged from the tube 19 to provide a quick expansion of the penis base tissue (the part which is most sensitive to the effect of the air subpressure) and thus obtain its closing upon the front-labyrinth labyrinth elastic seal ring 10, i.e. to provide a good sealing between the neck of the tube and the seal ring 10 what is essential for the further development of the penis erection achieving process.

In the second phase of this process the cavernous tissue all over the penis length receives blood, i.e. gets filled. This phase of making the erection must, for physiological reason, run slowly to enable the cavernous tissue of the penis to absorb blood gradually and wholly and, the lower air the pressure in the tube is (i.e. the higher the level of filling of the cavernous tissue with blood in the penis is), the slower this phase must run.

In the third, final phase of this procedure—i.e. when the subpressure in the tube 19 reaches the lowest (prescribed) value, the sucking of the air out of the tube 19 must fully and safely stopped. The penis is kept in such 'environment' until it has reached its full length, i.e. until it has achieved a full erection.

All the phases of the procedure for achieving the erection of the penis according to the presented programme must be done faultlessly by the use of the air discharge regulator 1, 4, 5 provided within this apparatus.

A ring-shaped filter 18 is disposed in the expanded part of the head 17 and it prevents possible direct penetration into the sensitive parts of the mechanisms of the head 17 and the pump 15. The head 17 also houses a valve 3 which is provided for the purpose of the manual letting in of the outside air into the tube 19 of the apparatus after having achieved the erection so that the penis can be taken out of the tube 19. This valve 3 opens by pressing onto its cap or push button 2 so that the outside and the inside air pressure get equalized and the penis can be taken out of the apparatus.

The bellow pump 15 comprises an elastic bellows 14 reinforced by a spring 13 from the inside to increase the tension of the expanding of the bellows 14, as well as an inlet valve 12 and an outlet valve 11. It is connected to the head 17 of the apparatus by means of a threaded connection fitted with an elastic seal ring. The working volume of this pump 15 should be at least 25 cm$^3$ and the pump should be capable to produce a subpressure of at least −40000 P.

FIG. 4–7 show the elastic ring 9 for tightening and locking the base of the penis, FIG. 5 being a longitudinal section along the lines C—C of FIG. 6. FIG. 7 shows cross sections of the ring in the FIG. 5 and 6.

This elastic ring 9 is formed by an elastic ribbon of a round section, fitted with a small ball 23 at one end and a profiled opening 27. At the other end, the ribbon is provided with a semi-round small head 24.

When making this ring, the little ball 23 and a part of the elastic ribbon disposed between the little ball and the opening 27, and a part of this opening must be reinforced with fibrous flexible spinning-material 25. Also, the head 24 and a part of the elastic ring 9 must be reinforced with flexible fibrous material 25. The ends of the ring 9 are reinforced to make them less elastic because it is essential for easy releasing and unlocking for the ends of the ring 9 at the required moment, i.e. at the moment just before the ejaculation.

The embodiment of the apparatus for achieving and maintaining the erection of the penis described above functions as follows:

After the penis has been inserted into the tube 19 so that the seal ring 10 at the neck of the tube fits tightly onto the base of the penis, the air pressure in the tube 19 is reduced by periodically pressing on the bellows 14 of the pump 15 as far as the spring 13 allows and allowing the bellows 14 to return back to the original position under the pressure of the spring 13.

The pump 15 will during this operation with the help of the intake valve 12 and the outlet valve 11 suck out the air from the tube 19. During this (initial phase) of the procedure for achieving the erection, the regulator valve 4 is fully open. The sucked air passes freely from the tube 19 through the opening in the piston 1 of the regulator, through the borehole 16, through the pump intake valve 12, and through exhaust valve 11 of this pump and is discharged into the atmosphere.

At this phase, the bellows 5 will extend a little depending on the obtained subpressure, but the flow of the air from the tube will be neither damped nor cut off.

As the procedure of pumping (further thinning of the air in the tube 19) is still continued, the second phase of the procedure for achieving the erection of the penis starts. The increasing reduction of the air pressure in the tube results in a corresponding extension of the bellows 5. Valve 4 is still open, but the piston head 1 more and more closes the opening of the borehole 16 and thus the flow of the thinned air is gradually damped and with decreasing air pressure in the tube 19, the air flow through the borehole 16 is increasingly throttled.

When an appropriate subpresssssure is reached in the tube 19, the third phase of the penis erection achieving procedure is started: The bellows 5 are fully extended, the valve 4 is fully closed, the specified subpressure is constantly maintained (the patient cannot influence it by his will) and the penis achieves the final erection. This specified subpressure may be in the range of −10,000 to −27,000 P.

After having achieved the penis erection in this way, the procedure for maintaining the achieved erection is started. The lever 20 is shifted by hand in the F direction (FIG. 1) thereby pressing with its projections 21 against the bushing 22 which then, with its head 8 pushes the elastic ring 9 for tightening the base of the penis until it slips from the neck of the tube 19 onto the base of the penis which is in full erection. Pressing the push-button 2 of the valve 3 will let outside air into the tube 19, the inside and the outside pressure will equalize, and the penis can be taken out of the tube. As the elastic ring 9 remains at the base of the penis, the blood will be prevented to flow out of it and the erection will be maintained during the intercourse.

At the end of the intercourse, just before ejaculating, the little ball 23 of the elastic ring 9 is pulled in the E direction (FIG. 3) without taking the penis out of the vagina of the woman.

Then the elastic ring 9 should be released by unlocking its ends. The penis will be quickly released from the tightening ring 9 and the semen will be expelled without any hinderence.

Shortly speaking, without excessive explanations, the apparatus is used in the following way:

The penis is inserted into the tube 9 of the apparatus;

The bellows of the pump 15 are depressed and released periodically until the penis reaches its full length;

The lever 20 is shifted in the F direction as far as it can go;

The press-button 2 is pressed for 2 to 3 seconds;

The penis is taken out of the tube 19 of the apparatus.

We claim:

1. Apparatus for achieving and maintaining penis erection based on the effect of reduced air pressure on the external surface of the penis, said apparatus comprising an elongated tube (19) having an open end for receiving the penis and a closed end; a head (17) attached to said closed end of said tube; a vacuum source (15) attached to said head (17); a valve (4) in said head (17) for regulating air pressure in said tube (19), said valve (4) having a piston (1) which is in air communication with said vacuum source (15) through a small tube (16) for reducing air pressure in said elongated tube (15); a lower end of said valve (4) being movably connected to an elastic bellows (5) filled with gas in order to move said piston (1) which regulates the quantity of air pumped out through said small tube (16) by said vacuum source (15).

2. The apparatus of claim 1 wherein said elastic bellows (5) is operatively associated with said valve (4) for closing said small tube (16) from said elongated tube (19) to said pump (15).

3. The apparatus of claim 1 wherein said head (17) further comprises a valve (3) actuated by a button (2) for permitting air into said elongated tube (19) and thus relieving the vacuum, permitting removal from the penis.

4. The apparatus of claim 1 further comprising an elastic seal ring (10), said seal ring (10) having an inside diameter which is varied to fit in accordance with the size of the penis, said elastic seal ring (10) to be placed inside said open end of said elongated tube (19), whereby it is possible to replace said seal ring (10) in said open end of said tube (19), said seal ring (10) further comprising frontal and labyrinth seals for sealing of the inflowing air around the base of the penis in said tube (19).

5. The apparatus of claim 4 wherein an external surface of said open end of said elongated tube (19) is provided with a moveable bushing (22) having a widened front part (8) on the side opposite to said head (17); a double manual lever (20), located on said tube (19) above said bushing (22), is provided with two projections (21) for pushing said bushing (22) towards said open end of said tube (19); and a ring (9) located on the outside of said tube (19) below said front part (8) of said bushing (22) adjacent to base of said penis whereby said bushing (22) is used to slide said ring off said tube (19) onto the penis.

6. The apparatus of claim 5 wherein said elastic ring (9) comprises an elastic ribbon of round profile having a small ball (23) at one end and, a semi-round small head (24) at the other end; an opening (27) on said elastic ribbon for said semiround small head (24) near the said small ball (23) and used for attaching or removing said ring (9); the end of said ring (9) around said small ball (23) being reinforced by a flexible thread (26), the end near said semiround small head (24) also being reinforced by flexible thread (25), the end of said ribbon of said ring (9) near said small ball (23) being slightly bowed toward the external part together with said small ball (23) to provide easier handling of the end of said ring (9) and its fast removal from the base of the penis.

7. The apparatus of claim 1 further comprising a filter (18) located inside said closed end of said elongated tube (19) and under said bellows (5).

8. The apparatus of claim 1 wherein said vacuum source (15) comprises a vacuum pump (15) with a bellows (5) and a spiral spring (13) and wherein said apparatus further comprises an inlet valve (12) and an outlet valve (11) located in located in said head (17) and adjacent said pump (15), said inlet valve (12) and said outlet valve (11) regulate flow of air to pump (15).

9. Apparatus for achieving and maintaining penis erection based on effect of the reduced air pressure on the external surface of the penis comprising an elongated tube (19) for receiving the penis, said tube (19) having an open end and a closed end; a head (17) attached to said closed end of said tube (19); a means (15) for reducing air pressure on the external surface of the penis attached to said head (17); and a filter (18) located in said head (17) between said reducing means (15) and said closed end of said tube (19).

* * * * *